(12) United States Patent
Neuss et al.

(10) Patent No.: US 7,070,614 B1
(45) Date of Patent: Jul. 4, 2006

(54) RADIALLY EXPANDABLE VESSEL SUPPORT

(75) Inventors: Malte Neuss, Rockumstrasse 20, D-53121 Bonn (DE); Michael Orlowski, Bonn (DE)

(73) Assignee: Malte Neuss, Bonn (DE)

( * ) Notice: Subject to any disclaimer, the term of this patent is extended or adjusted under 35 U.S.C. 154(b) by 0 days.

(21) Appl. No.: 09/806,758

(22) PCT Filed: May 22, 2000

(86) PCT No.: PCT/EP00/04658

§ 371 (c)(1),
(2), (4) Date: Aug. 20, 2002

(87) PCT Pub. No.: WO00/71053

PCT Pub. Date: Nov. 30, 2000

(51) Int. Cl.
*A61F 2/06* (2006.01)

(52) U.S. Cl. ..................................... 623/1.15

(58) Field of Classification Search ............... 623/1.11, 623/1.14–1.21; 606/194
See application file for complete search history.

(56) References Cited

U.S. PATENT DOCUMENTS

| | | | | |
|---|---|---|---|---|
| 5,733,303 A | * | 3/1998 | Israel et al. ................ | 623/1.15 |
| 5,807,404 A | * | 9/1998 | Richter ....................... | 623/1.16 |
| 6,231,599 B1 | * | 5/2001 | Ley ............................. | 623/1.15 |
| 6,273,913 B1 | * | 8/2001 | Wright et al. ............... | 623/1.42 |
| 6,325,821 B1 | * | 12/2001 | Gaschino et al. .......... | 623/1.15 |
| 6,461,380 B1 | * | 10/2002 | Cox ........................... | 623/1.17 |
| 6,488,703 B1 | * | 12/2002 | Kveen et al. ............... | 623/1.15 |
| 6,602,281 B1 | * | 8/2003 | Klein ......................... | 623/1.15 |

FOREIGN PATENT DOCUMENTS

| | | |
|---|---|---|
| DE | 198 22 157 A1 | 5/1998 |
| WO | WO 99/17680 | 10/1998 |
| WO | WO 00/06051 | 7/1999 |

\* cited by examiner

*Primary Examiner*—Alvin J. Stewart
(74) *Attorney, Agent, or Firm*—Reed Smith LLP; Stanley P. Fisher, Esq.; Juan Carlos A. Marquez, Esq.

(57) ABSTRACT

The invention relates to a radially expandable vessel support which comprises a multitude of zigzag shaped annular elements interconnected in a flexible way by bending elements. Said annular elements define a vessel support with a proximal and a distal end and a longitudinal axis, where the zigzag shaped annular elements are arranged side by side across the longitudinal axis of the vessel support, where zigzag shaped annular elements are linked to at least one further annular element by means of at least one bending element which is comprised either of a pair of S-shaped bars or of a pair of bow shaped bars which are located diametrically on the circumference and whose apertures show into opposite directions.

20 Claims, 8 Drawing Sheets

Fig. 3
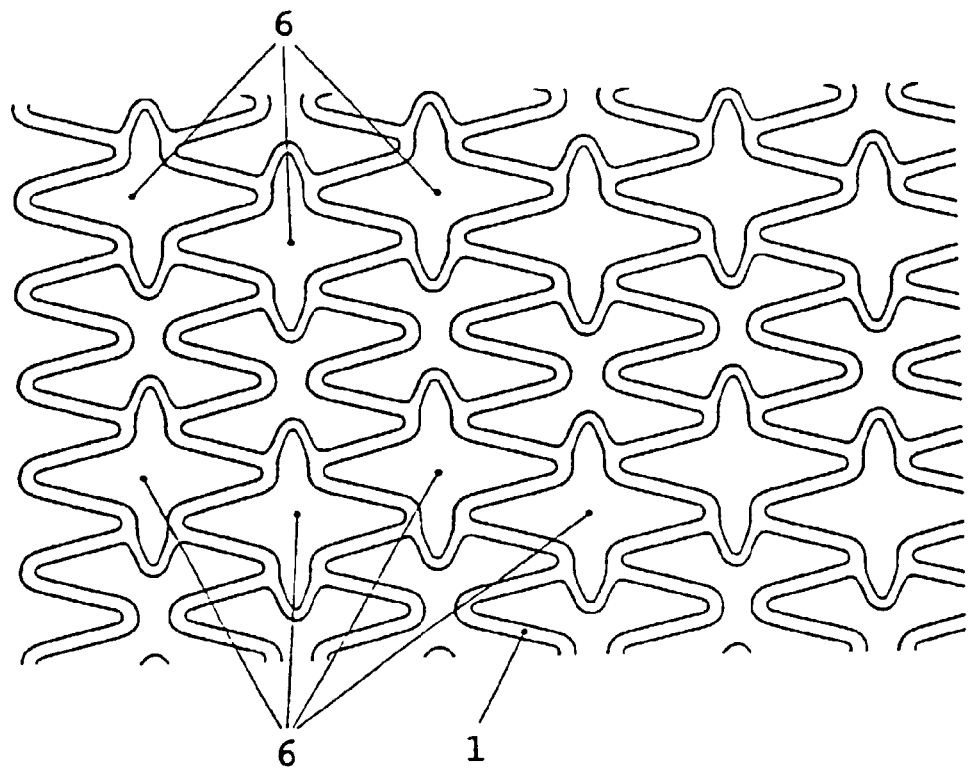
Fig. 4
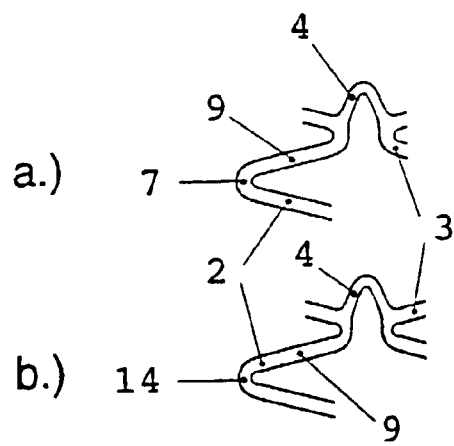
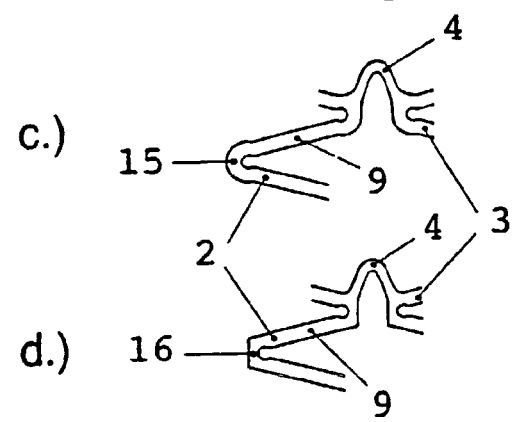

Fig. 6
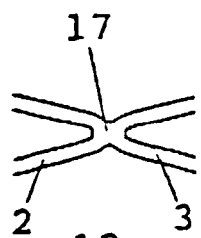
a.)
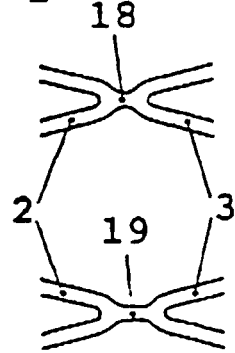
b.)
c.)
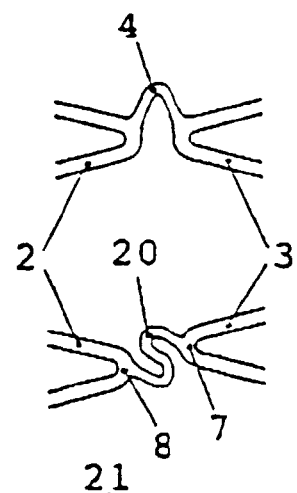
d.)
e.)
f.)
g.)
h.)

RADIALLY EXPANDABLE VESSEL SUPPORT

The invention relates to a radially expandable vessel support to be used for keeping open blood vessels or other paths of organs in human or animal bodies. This grid shaped vessel support consists of several tubular elements with a zigzag shaped annular structure of small width which are linked by bow shaped or S-shaped bars.

In the patent EP 335 341 B1 vessel supports are described which are formed from elongated pairs of members. These vessel supports are implanted for example in contracted or other body vessels to keep them permanently open after a balloon dilatation. The vessel supports are thereby expanded in their diameter and contract in their sidewise length. As a rule, this contraction is undesirable, since it can cause an erroneous positioning of the vessel support. The known vessel supports adapt themselves relatively poorly, or not at all, to bows or curves in the course of the vessel, such that additional bending elements must be provided for.

The known vessel supports exhibit rigid tubular segments which are linked up somewhat more pliably by flexible connecting pieces. However, in these sectors hypertrophies of the vessel wall may occur through that because of the particular strain put on the wall by every movement of the vessel. Other known vessel supports exhibit a considerable contraction, especially if expanded in the regime of their maximum diameter.

Vessel supports have been known for example from patent DE 197 40 506 A1 with bars, having the shape of bows and being oriented in the same direction, between the zigzag shaped annular elements. However, due to the numerous bars between the annular elements that vessel support is very rigid and inflexible which can lead to a failure when implantation is attempted in the case of a curved course of the vessel.

Due to the numerous bow shaped bars, side arms of the vessel system which should remain open may be blocked inadvertedly.

Because of the bow shaped bars on the circumference, being oriented in the same direction, there is also the disadvantage that this vessel support does easily bend when the course of the vessel is curved, and blocks, in part or completely, the vessel which was meant to be kept open with the vessel support.

It is the task of the present invention to create a radially expandable vessel support which does exhibit no, or only a minor, contraction during its expansion; which does bend less easily while being better suited to a curved course of the vessel; and exhibits a sufficient radial stability. Also, the vessel support should exhibit, in its expanded state, cross sections between the individual bars that are sufficiently large for the side branch exits of the vessel system to remain open.

This task for said vessel support is solved by linking zigzag shaped annular elements with at least one further by means of at least one bending element which consists either of a pair of bow shaped bars which are located diametrically on the circumference and whose apertures point into opposite directions, or of a pair of S-shaped bars.

Upon radial expansion of the vessel support, the bars will stretch along the longitudinal axis, corresponding to the sidewise contraction of the zigzag shaped annular elements, thus avoiding or reducing an overall contraction of the vessel support. In accordance with the invention, the bow shaped bars are arranged at one or several annular elements in pairs in opposite directions, resulting in either a star shaped appearance or a particularly advantageous bending element. Likewise, S-shaped bars are arranged in pairs; however the arrangement in opposite directions is not necessarily required here, even though it is the preferred arrangement. In spite of high flexibility a high radial stability results from the multicellular structure, which can be further enhanced by arranging, in a spiral shape or alternatingly, for example one or several star shaped segments. In order to further increase the flexibility of vessel supports individual segments may, for example, be linked up with only two bow shaped bars whose apertures point into opposite directions, or with S-shaped connecting bars. According to dimension, number, arrangement and form of such connecting bars the bending behavior of the vessel support as a whole will be further influenced.

The following shapes and combinations may be considered for the connecting bars: X-shaped or dumb-bell shaped bar, straight or bow shaped bar, S-shaped bar or a bar in the shape of a sinusoidal wave, or a straight and bow shaped bar.

The bar between the individual annular elements preferably exhibits a somewhat reduced cross section (about 30%) as compared with the straight bar of the zigzag shaped annular elements.

Upon radial expansion of the vessel support e.g. the star shaped segments are distorted, thus creating an aperture which is approximately rhombic which can be post-dilated favorably for the sidewise exit of vessels, and through which the implantation of a further vessel support in a side arm may be effected. Between two star shaped segments at least one arch of the zigzag shaped annular element must remain free, without a lateral connection to the next annular element, such that the bow shaped bars of the star shaped segment will not obstruct one another upon mechanical compression of the vessel support e.g. on a balloon, and that the profile of introduction remains as small as possible for implantation into the body through an introductory lock.

Furthermore, the zigzag shaped annular elements may exhibit different cross sections at the edge and in the central range. To improve the supporting properties and radial strength at the edge, the vessel support may exhibit a larger width of the bars at both ends. To improve the local supporting properties in the area of a focal vessel narrowing and the radial strength, the vessel support may exhibit a larger width of the bars and/or a larger cross section and/or more linking bars in the central range only. The larger cross section in the central range may be achieved e.g. through an electro-polishing process which will remove less material.

In order to further increase the flexibility, several segments of the vessel support may be linked in pairs by two bars in the shape of bows, or some other shape, which are opened in opposing directions.

The vessel support's bending behavior upon crimping and expansion may be further improved by providing a particular shape of the arches of the zigzag shaped annular elements, for example C-shaped, or the shape of a hairpin or bracket, especially if the width of the C-shaped or bracket shaped arch is smaller than that of the bar of the zigzag shaped annular element.

As material for the vessel support, preferably one or more biocompatible metals may be used of the group niobium, platinum, steel, titanium, a nickel-titanium alloy, platinum-iridium, or an alloy made from at least one of these metals like platinum-iridium with suitable weight percents. If the vessel support is to be self expandable, a nickel-titanium alloy is preferably used which is temperature optimized by heat treatment.

In order to improve the growth into the vessel wall, the metal may be coated with a biocompatible material or with suitable medicaments to avoid hyper-proliferation of the vessel, or may produce a radiation by irradiation or radioactive decay.

Furthermore the vessel support may consist of a resorbable plastic material, for example aliphatic polyesters like polydioxanon.

If the vessel support is to be used for the bracing of aneurysms, it is preferably provided with a biocompatible fabric braided or sewn onto it, made from polyurethane, silicone, Teflon or polyester, or a thin foil made from one of these materials is sewn, welded, shrunk or glued to it.

The tubular bodies of metal or plastic are preferably formed from seamlessly drawn tubes in order to avoid stress and cracks, as would be the case in the vicinity of welding seams. The structures are preferably produced by laser beam cutting, water jet cutting, electro-erosion and electro-polishing.

In the following embodiments of the invention are further explained with the aid of a diagram. In this diagram, FIG. 1 shows, in a representation of the unrolled basic pattern, an embodiment of the present invention with star shaped segments in the non-expanded state.

FIG. 3 shows an alternative embodiment of the present invention with star shaped segments in the non-expanded state which are arranged side by side, obliquely above and below in an alternating fashion.

FIGS. 4a–d shows different embodiments of the zigzag shaped annular elements.

Figure 5:
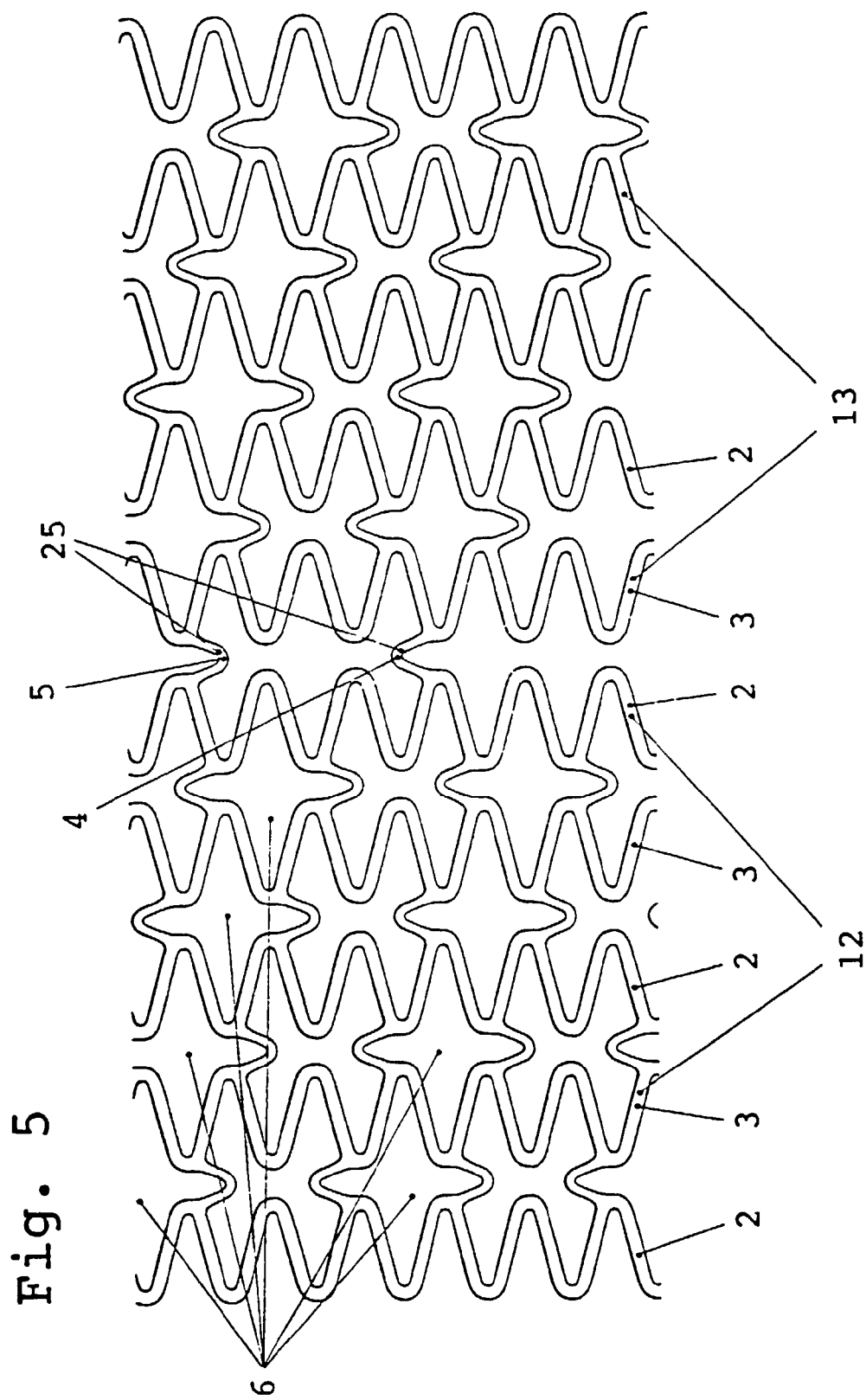

FIG. 5 shows a further alternative embodiment of the present invention with star shaped segments arranged spiraly, sloping one below the other, with a flexible link of two sectors by means of two bow shaped bars.

FIGS. 6a–h shows linking elements of various shapes between sectors.

Figure 7:
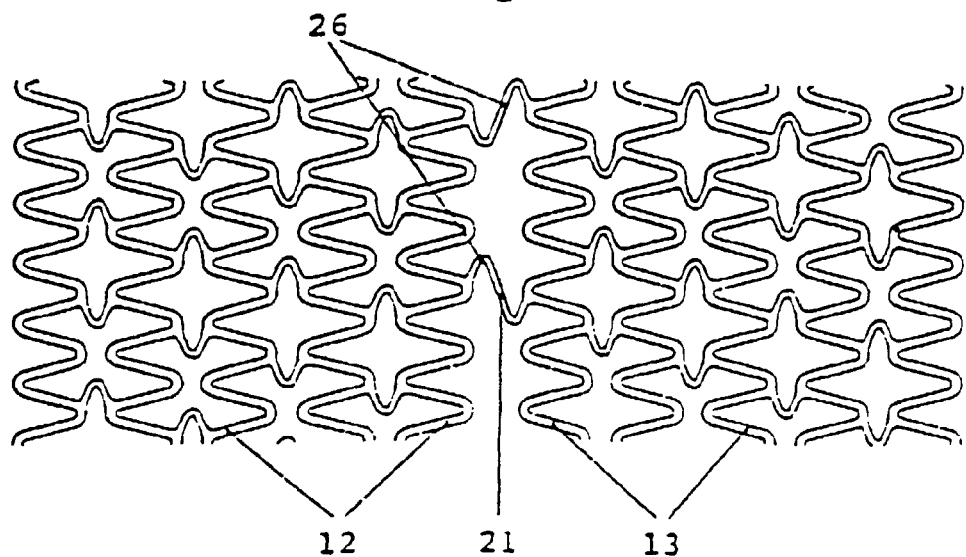

FIG. 7 shows a further alternative embodiment of the present invention with star shaped segments arranged spiraly, obliquely one below the other, with a flexible S-shaped bar connection between two sectors.

Figure 8:
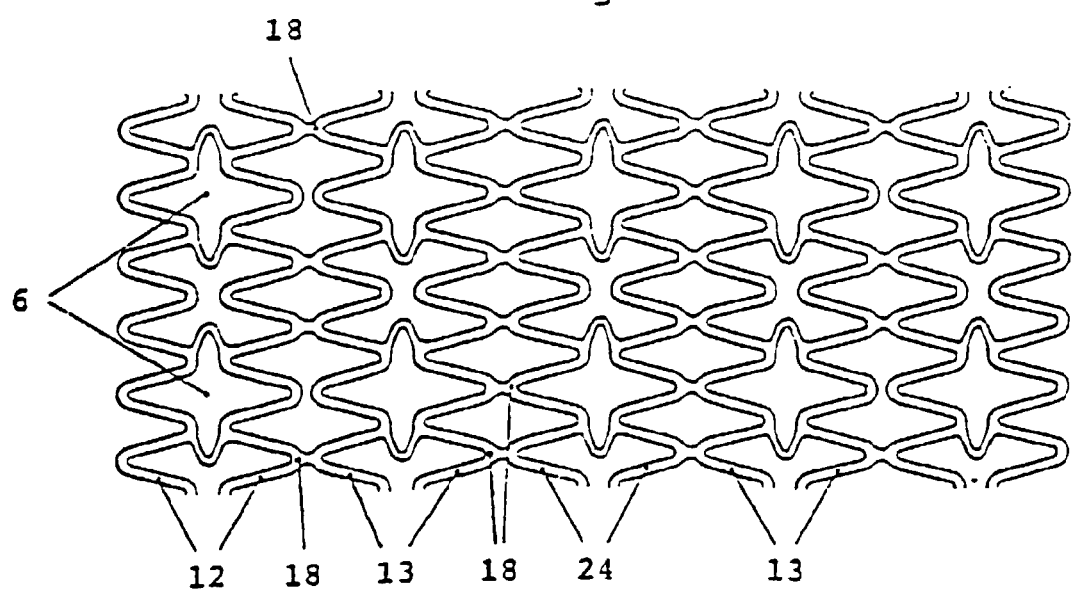

FIG. 8 shows a further alternative embodiment of the present invention with star shaped segments arranged in parallel, with dumb-bell shaped bar connectors between the sectors which consist of star shaped segments.

Figure 9:
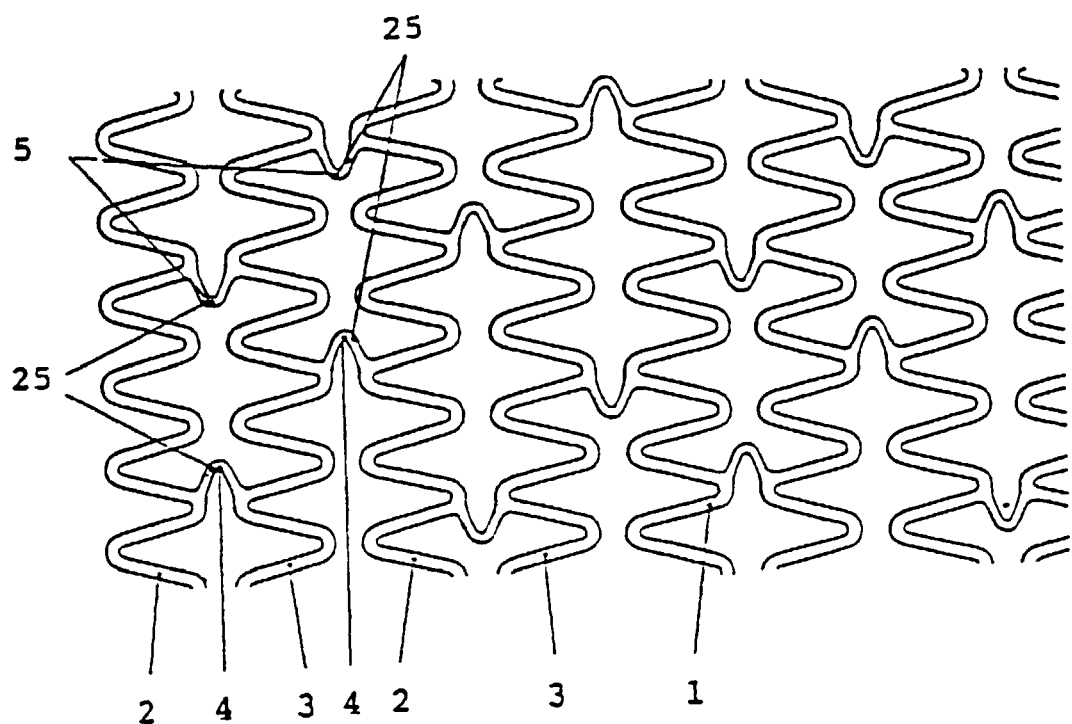

FIG. 9 shows, in a representation of the unrolled basic pattern, part of an embodiment of the present invention with bow shaped pairs of bars in the non-expanded state.

Figure 10:
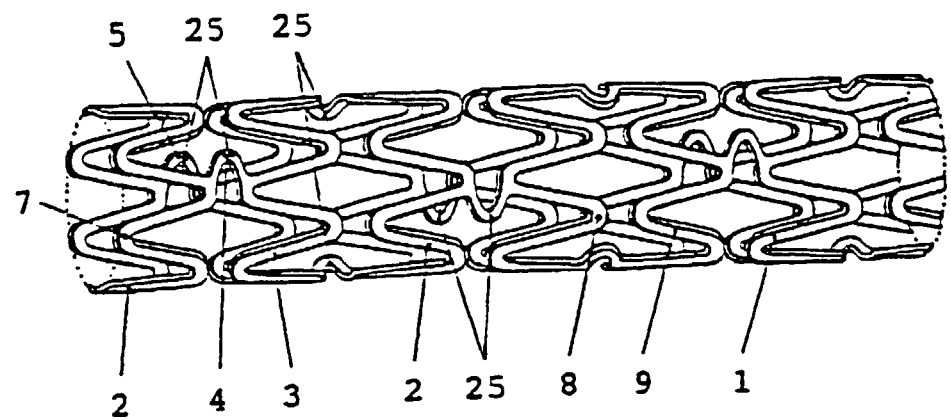

FIG. 10 shows a side elevation of the tubular vessel support of FIG. 9 with the bow shaped pairs of bars characteristic of the invention, in the non-expanded state.

Figure 11:
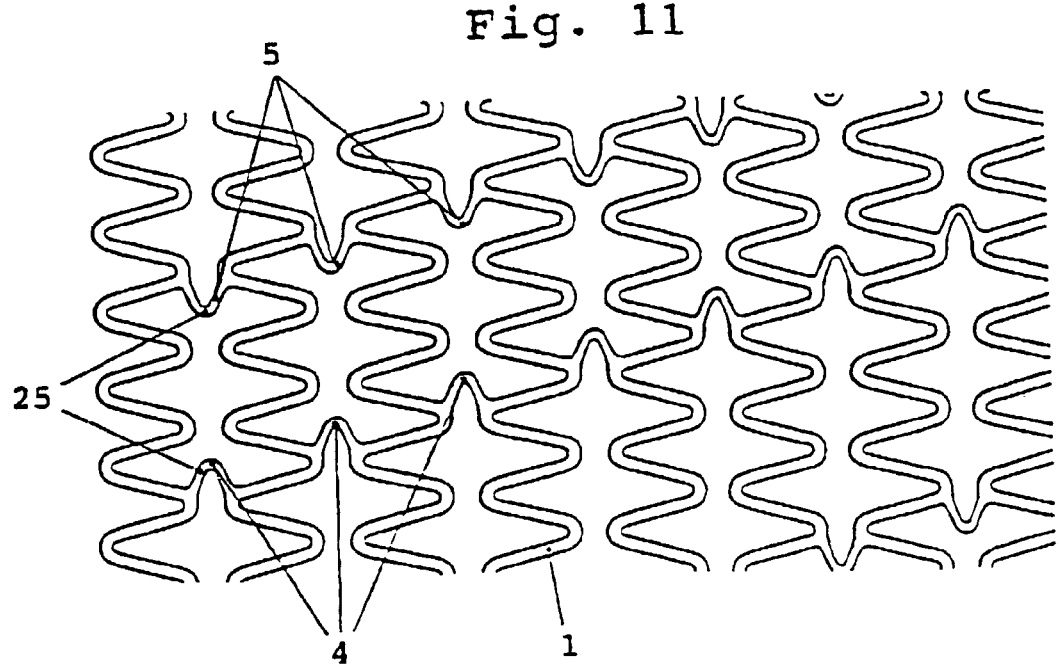

FIG. 11 shows a further alternative embodiment of the present invention with bow shaped pairs of bars arranged spiraly and obliquely.

Figure 12:
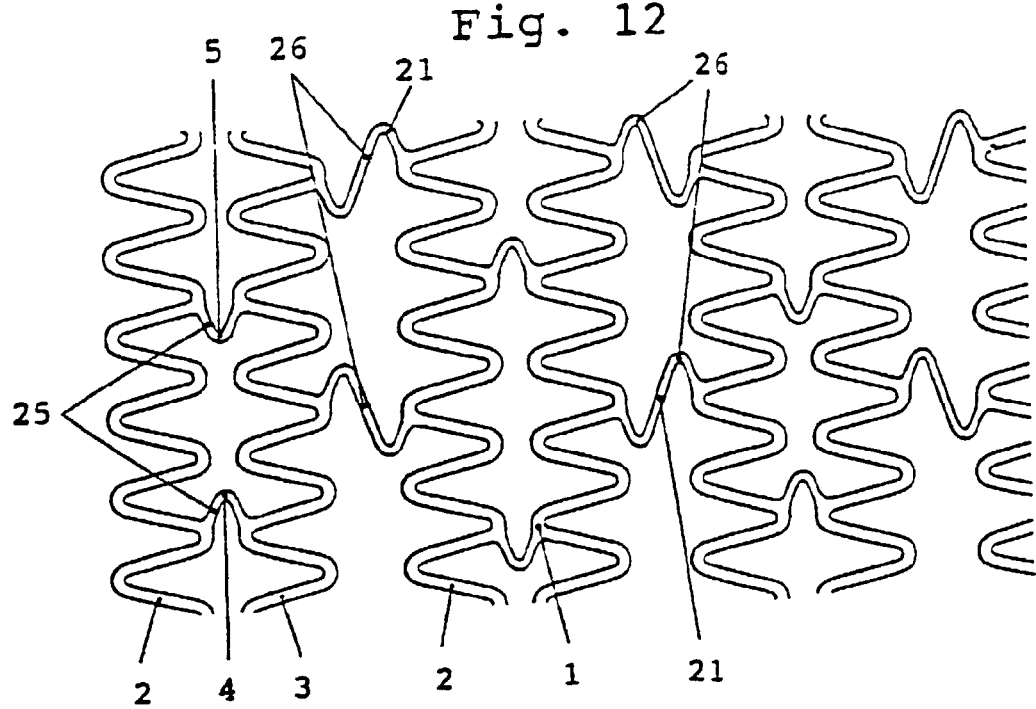

FIG. 12 shows a further alternative embodiment of the present invention with pairs of bars that alternately are bow shaped and more flexible in the shape of a sine wave.

Figure 13:
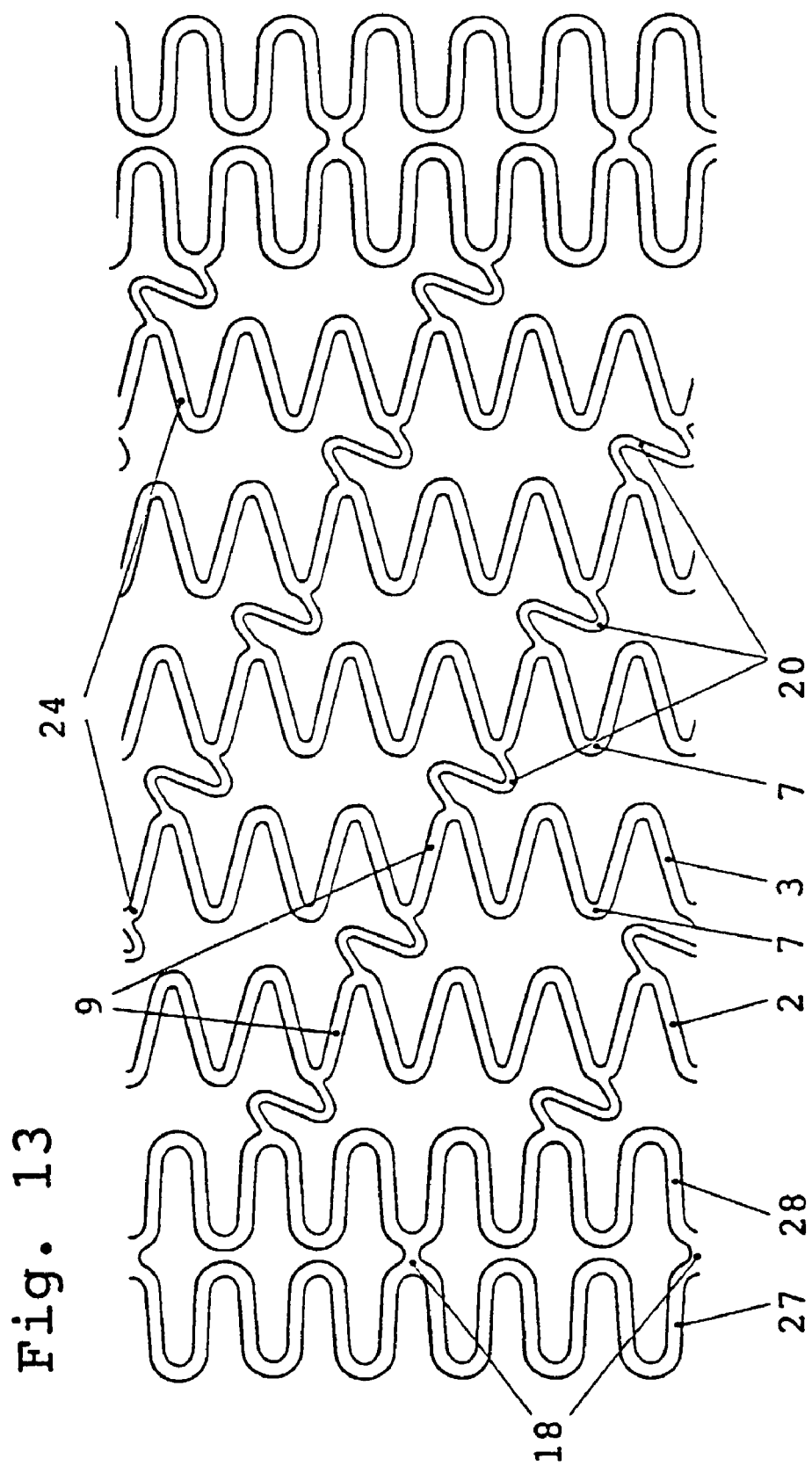

FIG. 13 shows a further embodiment with snake shaped annular elements linked by dumb-bell shaped bars in the outer range, and zigzag shaped annular elements linked by more flexible S-shaped bars in the central range.

The vessel supports shown in the figures exhibit zigzag shaped annular elements with star shaped segments and linking elements of a different shape. For the sake of clarity only examples of unrolled grid structures of the tubular vessel support, or parts thereof, are shown in the figures.

Figure 1:
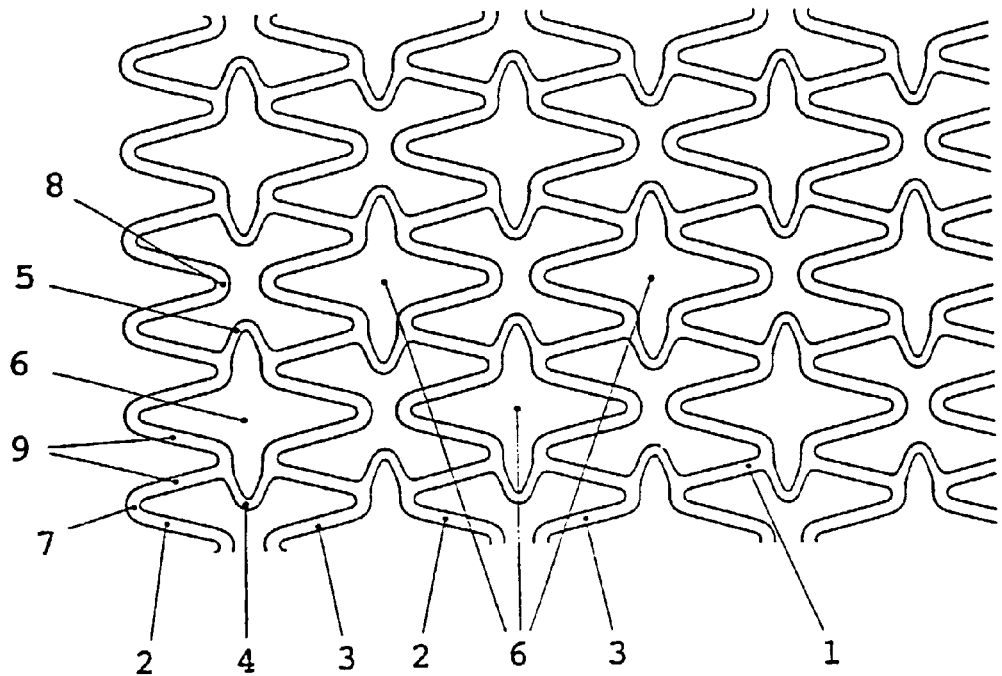

In the vessel support 1 shown in FIG. 1 zigzag shaped annular elements 2 and 3 are linked up to star shaped segments 6 by bow shaped bars 4, 5. The connection to the nearest lateral zigzag shaped annular element 2 is also made with a star shaped segment 6 which is arranged laterally between the two star shaped segments 6, etc.

In the embodiment shown the vessel support 1 consists of zigzag shaped annular elements 2, 3 with 6 each of arches that are alternately open to the right 7 and the left 8, linked up with bars 9 in a zigzag shape.

Figure 2:
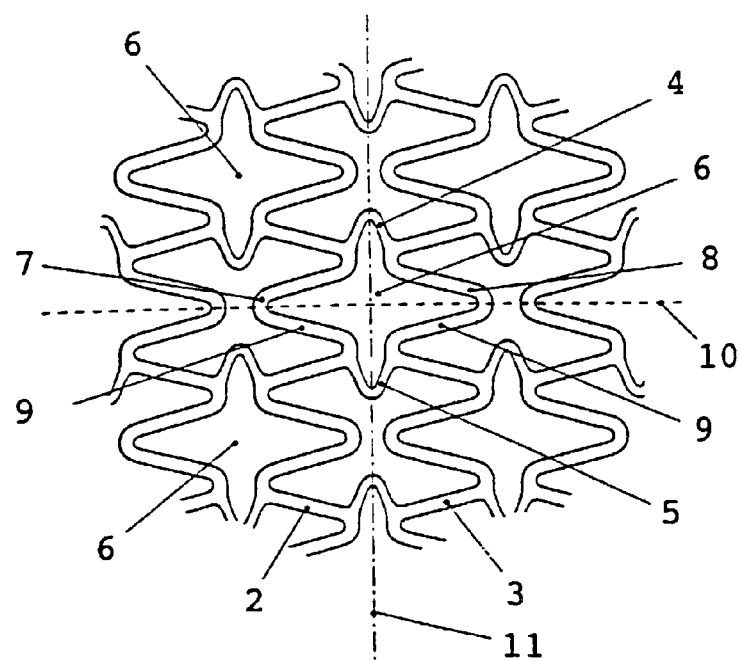
FIG. 2 shows a sector of FIG. 1 with the star shaped segment characteristic of this invention.

FIG. 2 shows a sector of FIG. 1. The zigzag shaped annular element 3 corresponds to the zigzag shaped annular element 2, mirrored on an imaginary transversal axis 11. The bow shaped bar 4 arching upwards corresponds to the u-shaped, bow shaped bar 5, mirrored on a longitudinal axis 10 that is formed by the arch 7 of annular element 2, which is open to the right, and the arch 8 of annular element 3, which is open to the left. The bow shaped bars 4, 5 which are each arranged in pairs, together with arch 7 which is open to the right, and arch 8 which is open to the left, and the bars 9 of annular elements 2, 3, form two star shaped segments 6 on a longitudinal axis 10, or on the circumference of the tubular vessel support, respectively.

In the preferred embodiment, the width of the bow shaped bars 4, 5 is 10 to 50% smaller than the width of a straight bar or portion of the zigzag shaped annular elements 2, 3.

The star shaped segments 6 between the lateral sequence of annular elements 2, 3 are each arranged laterally between the previous star shaped segments 6.

FIG. 3 shows an embodiment similar to FIG. 1, however with star shaped segments 6 which are arranged, side by side, laterally in an alternating fashion obliquely below and obliquely above, on an imaginary longitudinal axis of the vessel support 1.

FIG. 4a shows an embodiment of the zigzag shaped annular elements 2, 3 with an arch 7, which is open to the right, and a bow shaped bar 4. Here, the width of arch 7 corresponds to the width of bar 9.

FIG. 4b shows a further embodiment of the zigzag shaped annular elements 2, 3 with a C-shaped arch 14, which is open to the right, and a bow shaped bar 4. Here, the width of arch 14 is smaller than the width of bar 9.

FIG. 4c shows a further embodiment of the zigzag shaped annular elements 2, 3 with a hairpin shaped arch 15, which is open to the right, and a bow shaped bar 4. Here, the width of arch 15 corresponds to the width of bar 9.

FIG. 4d shows a further embodiment of the zigzag shaped annular elements 2, 3 with a bracket shaped arch 16, which is open to the right, and a bow shaped bar 4. Here, the width of arch 16 is smaller than the width of bar 9.

FIG. 5 shows an embodiment similar to FIG. 3, however, the star shaped segments 6 are arranged between the zigzag shaped annular elements 2, 3 on an imaginary longitudinal axis laterally, sloping one below the other, in the shape of a spiral. Furthermore, several annular elements 2, 3 linked by star shaped segments 6 form a sector 12 which, in order to increase flexibility, is linked, according to the invention, to another sector 13 only by two bow shaped bars 4, 5 which are on opposite sides of the circumference and which will, according to the invention, form a bending element 25 which is open to the same direction.

FIG. 6a shows an X-shaped bar 17 between the zigzag shaped annular elements 2, 3.

FIG. 6b shows a dumb-bell shaped bar 18 between the zigzag shaped annular elements 2, 3.

FIG. 6c shows a straight bar 19 between the zigzag shaped annular elements 2, 3.

FIG. 6d shows a bow shaped bar 4 between the zigzag shaped annular elements 2, 3.

FIG. 6e shows an S-shaped bar 20 between the zigzag shaped annular elements 2, 3. The S-shaped bar 20 is arranged between arch 8, which is open to the left, and arch 7, which is open to the right. The arches 7, 8 preferably are located at different heights.

FIG. 6f shows a bar 21, in the shape of a sine wave, between the zigzag shaped annular elements 2, 3.

FIG. 6g shows a straight and bow shaped bar 22, as a combination of FIGS. 6c and 6d, between the zigzag shaped annular elements 2, 3. The bar 22 is arranged between arch 8, which is open to the left, and arch 7, which is open to the right.

FIG. 6h shows a straight and bow shaped bar 23, similar to FIG. 6g, with an elongated straight section; however, bar 23 is arranged, on the left, on the inside of arch 7 of the zigzag shaped annular element 2, which is open to the right; and on the right, on the outside of arch 7 of the zigzag shaped annular element 3, which is open to the right.

FIG. 7 shows an embodiment similar to FIG. 5, however, the two sectors 12, 13 are linked with a bending element 26 made up from bars in the shape of a sine wave.

In FIG. 8, a further alternative embodiment of the present invention is shown, with star shaped segments 6 arranged in parallel. Here, each sector 12, consisting of star shaped segments 6, is linked to the sector 13, which follows laterally, by means of several dumb-bell shaped bars 18. Between the central range 24 and the adjoining sectors 13, a dumb-bell shaped bar 18 may also be arranged.

In the vessel support 1 shown in FIG. 9 zigzag shaped annular elements 2 and 3 are linked with bending elements 25, which are formed by two each of bow shaped bars 4, 5 which are approximately on opposite sides.

In the embodiment shown the connection to the next zigzag shaped annular element 2 or 3, which is located laterally, is made by a further bending element 25 which is rotated by about 90°.

FIG. 10 shows a side elevation of FIG. 9. On the circumference, the zigzag shaped annular element 2, 3 consists of at least 4, preferentially even-numbered arches 7, which are open to the right, each being linked by a straight bar 9 with the same number of arches 8, which are open to the left. The bow shaped bars 4, 5, which are located in pairs diametrically on the circumference of the tubular vessel support 1 form a bending element 25 which is arranged with a displacement of about 90° with respect to the laterally adjoining one.

FIG. 11 shows an embodiment similar to FIG. 9, however, the bending elements 25 are arranged laterally sloping with respect to the previous bending element 25. Thereby the bow shaped bars 4, 5 which are arranged spiraly form a flexible, stable grid structure like a double helix on the circumference of vessel support 1.

FIG. 12 shows an embodiment similar to FIG. 9; however, according to the invention, bending elements 26 made from two bars in the shape of a sine wave, which are open in the same direction, are also arranged on the circumference of the vessel support 1, between the zigzag shaped annular elements 2, 3, in order to increase the flexibility in accordance with the invention, alternately instead of the bending elements 25 made from bow shaped bars 4, 5.

In FIG. 13 is shown a further embodiment of the invention, with snake shaped annular elements 27, 28 in the outer range which are linked by dumb-bell shaped bars 18, and zigzag shaped annular elements 2, 3 in the central range which are linked by more flexible S-shaped bars 20.

In this way, a still greater flexibility in the central range 24 is achieved. As a peculiarity of this picture, the arches 7 of the individual annular elements 2, 3, which are open to the right, are arranged on an equal level. Upon expansion of this structure, the individual bars 20 which will then expand, together with individual straight bars 9 of the zigzag shaped annular elements 2, 3, will form a revolving, stable double helix structure.

From the above description and from the examples of embodiment presented it becomes clear that the invention is not restricted to the combinations of features designated in the claims or the description, but rather that within the framework of the invention, other combinations of the features specified may be conceived.

LIST OF SYMBOLS FOR REFERENCE 1. vessel support
2. zigzag shaped annular element
3. zigzag shaped annular element
4. bow shaped bar
5. bow shaped bar
6. star shaped segment
7. bow which is open to the right
8. bow which is open to the left
9. bar
10. longitudinal axis
11. transverse axis
12. sector
13. sector
14. C-shaped arch
15. hairpin shaped arch
16. bracket shaped arch
17. X-shaped bar
18. dumb-bell shaped bar
19. straight bar
20. S-shaped bar
21. bar in the shape of a sine wave
22. straight and bow shaped bar
23. straight and bow shaped bar
24. central range
25. bending element
26. bending element
27. snake shaped annular element
28. snake shaped annular element

The invention claimed is:

1. A radially expandable intraluminal vascular support comprises a plurality of coupled flexible zigzag formed annular elements formed by straight bars of equal length and connected by arch portions therebetween, the zigzag annular elements being ordered vertically along a longitudinal axis, the zigzag formed annular elements define a proximal end and a distal end of the intraluminal vascular support, wherein in a non-expanded state each zigzag annular element is coupled to at least one other annular element through at least one opposing pair of bending elements, each of the bending elements being formed from a bow shaped connector bar connected between arch portions of adjacent zigzag annular elements, wherein portions of said adjacent zigzag annular elements and said bow shaped bars connected therebetween are arranged to form corresponding star shaped segments, wherein said at least one bending element, constructed from the bow shaped connector bars are ordered between the laterally following zigzag annular elements in a sloping, sequential spiral pattern so that the bow shaped connector bars give rise to a double helix structure over the length of the intraluminal vascular support.

2. A radially expandable intraluminal vascular support of claim 1, wherein the width of the bow shaped connector bars is 10 to 50% smaller than the width of a straight formed connector bar of the zigzag formed annular elements.

3. A radially expandable intraluminal vascular support of claim 2, wherein the width and/or the cross-section of the bow shaped connector bars, is greater on the proximal and distal ends of the intraluminal vascular support than in the middle section of the support.

4. A radially expandable intraluminal vascular support of claim 3, wherein the width and/or the cross-section of the bending elements, or the number of the bow shaped connector bars in the middle section is greater than that on the proximal and distal ends, which gives the middle section of the intraluminal vascular support a greater radial strength than the proximal and distal ends.

5. A radially expandable intraluminal vascular support of claim 2, wherein the width of the bow shaped connector bars is 30% smaller than the width of a strait formed connector bar of the zigzag formed annular elements.

6. A radially expandable intraluminal vascular support of claim 1, wherein at least one zigzag formed annular element is coupled to at least one other annular element through one pair of bending elements that consists of a pair of S-shaped bars.

7. A radially expandable intraluminal vascular support of claim 1, wherein at least one zigzag formed annular element is coupled to at least one other annular element through one pair of bending elements that consists of a pair of bow shaped bars curved in opposing directions and located on opposite sides of a circumference of the vascular support.

8. A radially expandable intraluminal vascular support of claim 7, wherein the width and/or the cross-section of the bow shaped connector bars is greater on the proximal and distal ends of the intraluminal vascular support than in the middle section of the support.

9. A radially expandable intraluminal vascular support of claim 8, wherein the width and/or the cross-section of the bending elements, or the number of the bow shaped connector bars in the middle section is greater than that on the proximal and distal ends, which gives the middle section of the intraluminal vascular support a greater radial strength than the proximal and distal ends.

10. A radially expandable intraluminal support of claim 1, wherein the bending elements, constructed from the bow shaped connector bars are ordered between the laterally following zigzag annular elements such that each is turned approximately 90° with respect to the longitudinal axis of the intraluminal vascular support.

11. A radially expandable intraluminal vascular support of claim 1, wherein in a middle section of each circumferentially placed bow shaped connector, the bow shaped connector bars are ordered in a sloping, sequential pattern, and that on both ends of a single bending element, which is constructed from two opposing H-shaped connector bars that are turned 90°, is placed between the middle section and the laterally following zigzag annular elements or the laterally followed spiral formed annular elements.

12. A radially expandable intraluminal vascular support of claim 1 is constructed from one or more of the metals of the group nickel, steel, titanium, tantalum, niobium, platinum, iron or tungsten, or an alloy of at least two of these metals.

13. A radially expandable intraluminal vascular support of claim 12 is constructed from alloy of nickel-titanium so that the support is self-expanding after heat treatment.

14. A radially expandable intraluminal vascular support of claim 1 is constructed from a resorbable synthetic material.

15. A radially expandable intraluminal vascular support of claim 1 is coated or covered with a thin walled foil of a biocompatible material.

16. A radially expandable intraluminal vascular support of claim 15, wherein the coating or cover releases radiation either through radioactive decay or irradiation.

17. A radially expandable intraluminal vascular support of claim 15, wherein the biocompatible material is a biocompatible fabric constructed from one or more polyurethane, silicone, Teflon, or polyester.

18. A radially expandable intraluminal vascular support of claim 1 is coated with medication so as to hinder the hyper proliferation of the vascular wall.

19. A radially expandable intraluminal vascular support of claim 18, wherein the medication coating is so constructed that the medication is slowly released in order to hinder the hyper proliferation of the vascular wall.

20. A radially expandable intraluminal vascular support of claim 18, wherein the coating or cover releases radiation either through radioactive decay or irradiation.

* * * * *